(12) United States Patent
Cremascoli et al.

(10) Patent No.: US 9,744,268 B2
(45) Date of Patent: Aug. 29, 2017

(54) BIOCOMPATIBLE AND BIODEGRADABLE COMPOSITE MATERIAL FOR USE IN SURGERY AND PROCESS FOR PRODUCTION THEREOF

(75) Inventors: Davide Cremascoli, Settimo Milanese (IT); Edgardo Cremascoli, Milan (IT)

(73) Assignee: NOVAGENIT S.R.L., Mezzolombardo (IT)

( * ) Notice: Subject to any disclaimer, the term of this patent is extended or adjusted under 35 U.S.C. 154(b) by 131 days.

(21) Appl. No.: 13/884,158

(22) PCT Filed: Nov. 11, 2011

(86) PCT No.: PCT/EP2011/069916
§ 371 (c)(1),
(2), (4) Date: May 8, 2013

(87) PCT Pub. No.: WO2012/062898
PCT Pub. Date: May 18, 2013

(65) Prior Publication Data
US 2013/0230572 A1 Sep. 5, 2013

(30) Foreign Application Priority Data
Nov. 12, 2010 (IT) .............................. MI2010A2106

(51) Int. Cl.
| | | |
|---|---|---|
| *A61L 27/44* | (2006.01) | |
| *A61L 27/58* | (2006.01) | |
| *A61L 27/48* | (2006.01) | |
| *A61L 27/18* | (2006.01) | |
| *A61L 27/22* | (2006.01) | |
| *A61L 27/24* | (2006.01) | |
| *A61L 27/54* | (2006.01) | |

(52) U.S. Cl.
CPC .............. *A61L 27/44* (2013.01); *A61L 27/18* (2013.01); *A61L 27/225* (2013.01); *A61L 27/24* (2013.01); *A61L 27/48* (2013.01); *A61L 27/54* (2013.01); *A61L 27/58* (2013.01)

(58) Field of Classification Search
None
See application file for complete search history.

(56) References Cited

U.S. PATENT DOCUMENTS

| | | | | |
|---|---|---|---|---|
| 2006/0141012 A1* | 6/2006 | Gingras | ..................... | A61F 2/08 424/442 |
| 2008/0220042 A1* | 9/2008 | Hashi | ..................... | A61K 38/58 514/1.1 |
| 2010/0330181 A1* | 12/2010 | Castiglione-Dodd | | A61K 9/0024 424/484 |
| 2011/0280921 A1* | 11/2011 | Giammona et al. | .......... | 424/423 |

OTHER PUBLICATIONS

Ding et al. "Immobilization of chitosan onto poly-L-lactic acid film surface by plasma graft polymerization to control the morphology of fibroblast and liver cells". Biomaterials, 2004, vol. 25 1059-1067.*
Wen et al. "Development of poly (lactide-co-glycolic acid)—collagen scaffolds for tissue engineering". Materials Science and Engineering C 27 *2007) 285-292.*
Sashiwa et al. "Chemically modified chitin and chitosan as biomaterials". Prog. Polym. sci. 29 (2004) 887-908.*
Olteanu "Applications of Functionalized Chitosan". Scientific Study & Research vol. 3 (2007) p. 227-256.*
Ganji et al. "Chitosan-g-PLGA copolymer as thermosensitive membrane". Carbohydrate polymers 80 (2010) 70-746.*
Olteanu et al. "Chitosan involved Tissue Engineering and Regenerative Medicine". 2007.*
Ungaro et al. "Bioactivated Polymer Scaffolds for Tissue Engineering". 2005.*
Riesenfeld, J. et al., "Quantitative Analysis of N-Sulfated, N-Acetylated, and Unsubstituted Glucosamine Amino Groups in Heparin and Related Polysaccharides", Anaylitical Biochemistry, Mar. 1990, vol. 188 pp. 383-389.
Yoo, H.S. et al., "Folate receptor targeted biodegradable polymeric doxorubicin micelles", Journal of Controlled Release, Feb. 3, 2004, vol. 96, pp. 273-283.
Ding, Z. et al., "Immobilization of chitosan onto poly-L-lactic acid film surface by plasma graft polymerization to control the morphology of fibroblast and liver cells", Biomaterials, 2004, vol. 25, pp. 1059-106T.
Duarte, A.R.C. et al., "Novel 3D scaffolds of chitosan-PLLA blends for tissue engineering applications: Preparation and characterization", The Journal of Supercritical Fluids, 2010, vol. 54, pp. 282-289.
Palumbo, F.S. et al., "New graft copolymers of hyaluronic acid and polylactic acid: Synthesis and characterization", Carbohydrate Polymers, 2006, vol. 66, pp. 379-385.

* cited by examiner

*Primary Examiner* — Robert A Wax
*Assistant Examiner* — Danah Al-Awadi
(74) *Attorney, Agent, or Firm* — Steinfl + Bruno LLP

(57) ABSTRACT

Composite biomaterials are described, which can be implanted in the human body in various branches of surgery or on the skin in dermocosmetic surgery, which can be formed as membranes or felts and which have properties of rate of absorption in the body and of hydrophilicity that can be modulated.

13 Claims, No Drawings

BIOCOMPATIBLE AND BIODEGRADABLE COMPOSITE MATERIAL FOR USE IN SURGERY AND PROCESS FOR PRODUCTION THEREOF

This application claims the benefit of priority to PCT Application No. PCT/EP2011/069916, filed Nov. 11, 2011, which claims priority to Italian Patent Application No. MI2010A002106, filed on Nov. 12, 2010. This and all other extrinsic materials discussed herein are incorporated by reference in their entirety.

FIELD OF THE INVENTION

The present invention relates to novel composite biomaterials for use in surgery, in particular in the form of membranes, as well as a process for production thereof.

PRIOR ART

In the course of surgical operations, and especially in post-operative applications, a vast range of materials is used, such as membranes, sponges, gauzes (or nets) and gels, which may be medicated or unmedicated (i.e. to which compounds with biological activity may or may not be added); all these materials will also be referred to hereinafter simply as "auxiliary surgical materials". Some examples of these materials are the antimicrobial medication AQUACEL® Ag of the company ConvaTec, or the gel OXIPLEX® of the company FzioMed, used for preventing surgical adhesions, in particular spinal ones, or the membrane SEPRAFILM® of the company Genzyme, used for reducing post-operative adhesions in abdominal or pelvic surgery.

The particular type of material to be used depends on the type of surgical procedure to be performed, or after which intervention is necessary. In some applications, which may require a second surgical procedure for removing the material applied, this must be biocompatible but not necessarily biodegradable (or absorbable); in other cases, both biocompatibility and biodegradability are required instead, especially in dermocosmetic surgery. Other characteristics that these materials may be required to have are adhesiveness or elasticity.

Non-absorbable materials currently commercially available include, for example, nets based on polyesters, polyamides or polypropylene, used in particular in urogynaecologic surgery; partially absorbable derivatives in the form of sponges, used in otorhinolaryngologic (or ENT, ear, nose and throat) surgery; or finally, absorbable materials such as gels or membranes based on modified and/or crosslinked hyaluronic acid, alone or in combination with other polymers, used mainly in dermocosmetic surgery. Examples of these materials are the MEROCEL nasal tampons from the company Medtronic or RADIESSE or RESTYLANE anti-wrinkle fillers (from the companies of the same names).

However, the materials currently available, further to having led to some highly contradictory results in clinical tests, have some contraindications connected with complications arising from their use.

The complications that can arise following surgery, due to application of the various materials, are varied and are often correlated with the nature of the material used or with the inflammatory reactions caused by their prolonged presence in situ; this is true in particular for devices that are biocompatible but not biodegradable, or for bioabsorbable materials that release inflammatory substances during degradation. For example, reactions of an inflammatory type are observed following the use of membranes (of PTFE or polypropylene), or in the case of nasal tampons for ENT surgery, removal of which often causes pain and bleeding.

As an alternative to synthetic materials for making surgical devices, it is possible to use natural polymeric materials, for example of the type produced by the human body, which therefore necessarily have the properties of being biocompatible and biodegradable. These materials must be selected from those that are able to form structures of sufficient mechanical strength. Of these materials, the most promising are collagen and fibrin. Collagen constitutes about a quarter of all the proteins in the human body, and is the most important structural protein; collagen forms molecular "wires" that reinforce tendons, as well as large, elastic sheets that support the skin and internal organs. Fibrin is a fibrillar protein, which polymerizes to form a mesh which, together with the platelets, constitutes the basis of the phenomenon of haemostasis. Another polymer endowed with structural consistency that can be considered for the production of surgical devices is chitosan, a polysaccharide of natural origin obtained by basic treatment of chitin, derived in particular from the exoskeleton of crustaceans.

However, these materials pose some problems for the production or in the use of surgical devices. Firstly, natural collagen and fibrin are characterized by very rapid absorption times, incompatible with the residence time necessary for performing the membrane functions in the surgical procedures mentioned above. Moreover, both collagen and fibrin, as well as chitosan, on account of their low solubility in the common solvents used in the synthesis of polymeric derivatives, are not easily processable for being transformed into auxiliary surgical materials.

The paper "Immobilization of chitosan onto poly-L-lactic acid film surface by plasma graft polymerization to control the morphology of fibroblast and liver cells", Z. Ding et al., Biomaterials, vol. 25, no. 6 (2004), pages 1059-67, describes composite materials comprising a synthetic polymer and a natural polymer (chitosan). The materials of this paper have some limits. In first place, in order to make possible the grafting of chitosan chains onto the poly-L-lactic acid (PLLA) film, this needs be pre-treated in an argon plasma and then exposed to the atmosphere to produce, on its surface, peroxide and hydroperoxide species capable of reacting with chitosan; these peroxide and hydroperoxide species, however, are free radicals and thus highly reactive, and can evolve in a non controlled way before conjugation with chitosan, possibly giving rise to noxious species thus making the composite not suitable for implantation in the human or animal body. Besides, as stated in the paper, the adhesion of cells on this film is poor, comparable to cell adhesion on glass; so, despite the indication in the paper that this material has potential uses in tissue engineering, said poor cell adhesion limits its applicability in the field of implants.

The aim of the present invention is to provide a new type of biocompatible and biodegradable material for use in surgery, that overcomes the problems of the prior art. In particular, the aim of the invention is to provide a biocompatible and biodegradable material suitable in particular (but not exclusively) for being formed into membranes.

SUMMARY OF THE INVENTION

This and other aims are achieved with the present invention, which in a first aspect relates to a composite biomaterial essentially consisting of a tridimensional structure made of a polymer chosen among collagen, fibrin and chitosan, to which are conjugated chains of a semi-synthetic polyester obtained from polymerization or copolymerization of at least a hydroxyacid chosen among lactic acid, glycolic acid or mixtures thereof.

The inventors found that conjugation of biodegradable polyesters to collagen, fibrin or chitosan makes it possible to modulate the absorption time of the composite materials obtained, prolonging it relative to the absorption time of collagen, fibrin and chitosan, making it possible to use devices obtained with these composites in surgery.

DETAILED DESCRIPTION OF THE INVENTION

The composite materials of the invention are formed from a polymer selected from collagen, fibrin or chitosan, which forms the tridimensional structure of the surgical device, on the surface of which chains of the aforementioned polyesters are conjugated; for this reason, collagen, fibrin and chitosan will also be defined as "structural polymers" in the rest of the description. These polymers have free amino groups, —$NH_2$, which can be made to react with suitably functionalized polyesters, obtaining the derivatized products of the invention.

The polyesters of the invention are synthetic polymers that are non-toxic, biocompatible and immunologically inert, which belong to the category of absorbable materials. Among the polyesters, polylactic acid is preferred.

Polylactic acid has been used since the 1990s in orthopaedic and odontostomatologic applications, and as filler in maxillofacial applications, and its use was approved in Europe in 1999 for cosmetic corrections of scars, of signs of ageing and of lipoatrophy due to antiretroviral therapies. This polyester is a bioactive material: through a mild but constant inflammatory reaction in the tissue into which it is injected, it in fact induces a progressive neosynthesis of collagen that leads to an increase and revitalization of the dermal thickness.

Hereinafter, the polylactic and polyglycolic acids will also be indicated, respectively, with the abbreviations PLA and PGA, and their copolymers will be indicated as PLGA.

In the present description and in the claims, the amount of polyester chains relative to the amount of the structural polymer is expressed as "derivatization degree"; this term means the value, as a percentage, of polyester chains bound in the composite biomaterial relative to the number of free —$NH_2$ groups in the initial structural polymer (i.e. the number of —$NH_2$ groups reacted relative to the total number of initial —$NH_2$ groups). The derivatization degree is determined by measuring the number of polyester chains bound in the composite biomaterial and the number of free —$NH_2$ groups therein. The number of bound polyester chains is measured by subjecting a portion of composite biomaterial to severe acid or basic hydrolysis (for example, with 6M hydrochloric acid or 3M sodium hydroxide at 70° C.), following which the polyester is liberated in its "reduced" form (lactic acid or glycolic acid); the amount of polyester is then measured by liquid chromatography. The number of free —$NH_2$ groups is measured by the method described in the article "*Quantitative analysis of N-sulfated, N-acetylated, and unsubstituted glucosamine amino groups in heparin and related polysaccharides*", J. Riesenfeld et al., Analytical Biochemistry 188, 383-389 (1990). The sum of the number of polyester chains and of free —$NH_2$ groups in the composite biomaterial is equivalent to the number of free —$NH_2$ groups in the initial structural polymer. Then knowing the number of polyester chains and the number of initial free —$NH_2$ groups, the derivatization degree, DD, is obtained from the formula:

DD=(number of bound polyester chains)/(number of initial free —$NH_2$ groups)×100.

The degree of derivatization with polyester of the structural polymer can vary widely, and is generally between 1 and 50%, and preferably between 5 and 30%. With a derivatization degree below 1%, the composite material has properties that do not differ substantially from those of the starting structural polymer, in particular as regards the rate of degradation in the organism, and therefore cannot be used for the purposes of the invention. Conversely, composite materials with a derivatization degree above 50% are difficult to produce and, in particular, are excessively lipophilic and are therefore less compatible with the environment of the organism, poorly absorbing organic fluids (generally water-based) with adverse effects on the material.

The properties of a specific composite material depend both on the nature of the structural polymer and of the polyester used, and on their relative amounts in the composite. In particular, as the derivatization degree increases, the resistance of the composite to biodegradation in vivo increases and its hydrophilicity decreases. With regard to biodegradation, the rate of the phenomenon varies with the derivatization degree because the presence of the polyester chains interferes with the action of the enzymes or cells that trigger the process of degradation of the matrix, leading to a slower absorption process than would occur with the structural polymer alone, said process involving both components of the composite material; on the other hand, the presence of the structural polymer leads to a higher rate of degradation than for the polyester alone. Consequently, a situation occurs in which each of the two polymers forming the composite material partially "transfers" its properties to the latter, leading to a material with intermediate characteristics relative to its starting components. Conversely, the decrease in hydrophilicity affects the capacity of the composite material to adsorb biological fluids. By controlling the derivatization degree it is thus possible for these characteristics to be finely tuned, to produce a composite that is suitable for the specific requirements of the application.

The composite materials of the invention are useful in particular for the production of medical and surgical devices in the form of membrane or felt, in which, as mentioned, the structural polymer constitutes the supporting structure of the device and the polyester determines its fine properties.

According to an alternative embodiment of the materials of the invention, the composites described above can be combined with other compounds having biological or pharmacological activity, obtaining a device that will be designated as "medicated" hereinafter. These further compounds can be, for example, agents that have antimicrobial activity, antifungal activity, antibiotic activity or other pharmacological activities.

Protein-based antibiotics and antifungals of the latest generation (antibiotics of this type are known as peptide or lipopeptide antibiotics) and growth factors based on glycoproteins are particularly suitable for combining with the structural polymer/polyester composites described above.

The peptide (or lipopeptide) antibiotics are particularly important as they do not appear to have the problem of development of resistance, after repeated use in therapy. This family includes, for example, but not only: daptomycin, meropenem, which are active against Gram-positive organisms; and PAC-113, an antifungal similar to histatin.

A non-exhaustive list of growth factors that can be conjugated to structural polymer/polyester composites includes: bone morphogenic proteins, known in this field as the BMP family, involved in processes of bone growth and of tissue growth in general, and in particular those known as BMP2 and BMP7; fibroblast growth factors (FGFs), active in angiogenesis, in wound repair and in embryonic development; vascular endothelial growth factors (VEGFs), active in angiogenesis; epidermal growth factors (EGFs), active in regulation of cellular growth, proliferation and differentiation; insulin-like growth factors (IGFs); platelet-derived growth factor (PDGF); and platelet factor 4 (PF4). These factors have been found to be of the utmost importance in initiating the various phases of the process of tissue regeneration of practically all animal tissues. To be able to incorporate these growth factors in a solid support proves to be very important for initiating tissue regeneration, at the very site of application.

Finally, the composite materials of the invention can be combined with drugs that do not react with the substrate but are simply incorporated in its three-dimensional solid network, for example in the pores of the structural polymer or of the final membranes or felts. These active principles are thus transported to the sites of tissue damage, where either tissue regeneration is required or there is an infection to be eradicated. These drugs can be for example conventional broad-spectrum antibiotics or those with specific action on MRSA (methicillin-resistant *Staphylococcus aureus*), on Gram-positive or Gram-negative organisms, on fungi or viruses. A non-exhaustive list comprises daptomycin, tigecycline, telavancin, bacitracin, streptomycin, isoniazid and vancomycin.

The concentration, relative to the total amount of composite, of active principles of the latter type can also be determined at the production site of the material and optimized according to the particular use for which the final surgical device is intended.

The pharmacological active principles conjugated to the structural polymer/polyester composites or those incorporated in the structure thereof exert their specific action at the site of application of the surgical device obtained from the composite; this can take place directly by contact, or more slowly at the time of release, as a result, for example, of degradation of the membrane structure.

An example of surgical device obtained with a composite of the invention is a membrane in which two different types of porosity are recognized, a three-dimensional part that is more porous, consisting essentially of the structural polymer, where the cells of the cartilage or the fibroblasts of the skin can enter to construct their natural matrix; this part is closely connected with the second, consisting essentially of the polyester, in which the pores are much smaller, so that the cells cannot pass through and travel to the lumen of the joint or to the surface of the skin. In this way the cells remain trapped in the biologically active three-dimensional scaffold, in an environment with ideal moisture content for growth and reproduction.

At the same time, the non-porous layer, orientated towards the lumen or the contaminated open air, constitutes a protective septum against contaminated dusts and therefore bacterial infections.

The product in the form of a membrane of the present invention can be obtained with various derivatization degrees between the two components. This condition makes it possible to have products with characteristics similar to native collagen or to natural fibrin, but with sufficient residence times for performing the functions required in the types of surgery mentioned above.

In a second aspect, the invention relates to a process for production of the composites already described.

The process consists of the following operations:
functionalization of the polyester with an activating agent of its free carboxyl group and subsequent purification of the product thus obtained;
reaction in heterogeneous phase between the solid structural polymer, which already has the desired final structure, and the functionalized polyester in solution in a polar aprotic solvent;
purification of the composite material obtained by treatment in aqueous or saline aqueous solutions.

For the reaction to be possible, it is necessary to use a solvent that is able simultaneously to wet the structural polymer and dissolve the polyester. Solvents suitable for the purposes of the invention are the polar aprotic solvents, including in particular dimethylsulphoxide (DMSO), N-methyl-2-pyrrolidone (NMP) and dimethylformamide (DMF).

The reagents used for the structural polymer are an unmodified natural collagen in lyophilic form, unmodified fibrin of animal origin (preferably of human origin), in the form of thin membrane or of three-dimensional coagulum, and chitosan in solid form, for example in lyophilized or in non-woven tissue form.

The polyester used is a commercial product of medical grade, ultrapure.

To facilitate the reaction of conjugation on the structural polymer of the polyester, the latter is first functionalized with activating agents of its free carboxyl group. Examples of said activation are the reaction with N-hydroxysuccinimide (NHS), according to the method described in the article "*New graft copolymers of hyaluronic acid and polylactic acid: Synthesis and characterization*", F. S. Palumbo et al., Carbohydrate Polymers, Vol. 66 (2006), pages 379-385; or according to the method described in the article "*Folate receptor targeted biodegradable polymeric doxorubicin micelles*", H. S. Yoo et al., Journal of Controlled Release, (2004) 96: 273-283; alternatively, the polyester can be activated by reaction with 1,1-carbonyldiimidazole (CDI), as is known by a person skilled in the art.

For carrying out the reaction, the activated polyester is dissolved in one of the solvents mentioned above; then the structural polymer selected is immersed in the solution thus obtained and it is left to react for a time between 1 and 15 hours, preferably between 2 and 6 hours, at a temperature generally between about 15 and 50° C.

At the reaction stage, the weight ratio between the starting polyester and the structural polymer is selected in relation to the desired derivatization degree in the final composite material, taking into account that the inventors have observed that the derivatization reaction has practically quantitative yield, i.e. essentially all the functionalized polyester used in the reaction binds to the structural polymer. Thanks to the particular type of reaction in heterogeneous phase it is possible to obtain multilayer solid preparations, in which every layer has different structural and microscopic characteristics depending on the use for which it is intended.

It is also possible to combine, in the phase of reaction between the structural polymer and the polyester, one or more agents with biological/pharmacological activity described previously, selected from peptide or lipopeptide antibiotics and growth factors. Association takes place by absorption and mechanical retention of these agents on the matrix of the structural polymer or, for high derivatization degrees with polyester, between the chains of the latter. In the first case, before submitting the structural polymer to the reaction in heterogeneous phase described above, the desired agents with biological/pharmacological activity are deposited thereon, and optionally the system is dried prior to reaction with the activated polyester. In the second case, said agents are adsorbed on the structural polymer/polyester composite already produced. In both cases, the kinetics of release of the agent with biological/pharmacological activity essentially follows the degradation of the composite.

At the end of the conjugation reaction, the composite obtained is purified simply by treatment in aqueous or saline aqueous solutions.

Once the composite material is obtained, comprising or not comprising the aforementioned pharmacologically active peptide (or lipopeptide) compounds, it is possible optionally to proceed with incorporation of further drugs or medicinal products in the composite, dissolving or suspending the latter in a solvent that is able to wet the composite, causing them to be adsorbed in the pores thereof, and finally removing the solvent, for example by evaporation at reduced pressure. The solvent in which this operation is performed can be the same medium used in the first reaction, if it is compatible with the selected pharmacological compound; alternatively, it is possible to dry the composite obtained from the structural polymer/polyester conjugation reaction (and optional peptide- or lipopeptide-type pharmacological agent) and soak it in a new solvent compatible with the selected pharmacological compound.

The invention will be further illustrated by means of the following examples.

EXAMPLE 1

Activation of Polylactic Acid with NHS (N-Hydroxysuccinimide)

The synthesis is carried out by the method described in the article of H. S. Yoo et al. cited above.

2.4 g of PLA of average molecular weight 8 kDa is dissolved in 30 ml of dichloromethane. First 0.25 g of the condensing agent dicyclohexylcarbodiimide (DCC), and then 0.14 g of NHS, are added to this solution, and left to react at room temperature for 24 hours. After this time, the reaction mixture is concentrated by partial evaporation of the dichloromethane and the product is precipitated in absolute ethanol and washed several times with the same solvent. The solid obtained is then filtered and dried under vacuum. A crystalline white solid is obtained, at a yield above 80 wt. % relative to the weight of the starting PLA. The $^1$H-NMR spectrum confirms that activation of the carboxyl group of PLA with NHS has taken place. The activation yield, expressed as ratio of moles of NHS bound to the moles of single chains of PLA, is 90%.

The $^1$H-NMR spectrum of the product PLA-NHS (CDCl$_3$) shows signals at: □ 1.5 and □ 1.6 (d, 3H, —O—CO—CH(CH$_3$)—OH; □ 3H, O—CO—CH(CH$_3$)—O—), □ 2.80 (m, 4H, —OC—CH$_2$—CH$_2$—CO—); □ 4.3 and □ 5.2 (m, 1H, —O—CO—CH(CH$_3$)—OH; m, 1H, —O—CO—CH(CH$_3$)—O—).

EXAMPLE 2

Activation of Polylactic Acid with CDI (1,1'-Carbonyldiimidazole)

1 gram of PLA with average molecular weight 8 kDa is dissolved at 50 mg/ml in DMSO. Then 40 mg of CDI is added. It is left to react at room temperature for 2-3 hours. The product is precipitated by pouring the solution directly into 100 ml of hexane. The precipitate is washed with two 50-ml portions of absolute ethanol. After filtration, the precipitate is dried under vacuum.

EXAMPLE 3

Preparation of a Membrane Based on Collagen Derivatized at 10% with Polylactic Acid A membrane in lyophilized form based on collagen with dimensions of about 25 cm$^2$ and with a thickness of about 5 mm, weighing 250 mg, is placed in a glass Petri dish. In a 10-ml glass test tube, 15 mg of activated polylactic acid (produced as described in example 1) is dissolved in 6 ml of DMSO. The solution is added directly on the surface of the collagen membrane in the Petri dish. The dish is closed and put in a stove at 40° C. and it is left to react for 4 hours. The dish is then taken out of the stove and the membrane is removed, and is immersed in a 500-ml glass beaker containing 300 ml of physiological saline at 0.9% NaCl. It is stirred gently for 2 hours. The operation is repeated once, stirring gently for 4 hours, and twice more using purified water instead of physiological saline. The membrane is removed and is left to dry in the stove at 37° C. for 24-48 hours. A sample of the product is measured for the derivatization degree, which is found to be equal to 10%.

EXAMPLE 4

Preparation of a Membrane Based on Collagen Derivatized at 20% with Polylactic Acid The procedure of example 3 is repeated, the only difference being that 30 mg of activated polylactic acid (produced as described in example 1) dissolved in 6 ml of DMSO is used for the derivatization reaction.

EXAMPLE 5

Preparation of a Membrane Based on Collagen Derivatized at 50% with Polylactic Acid The procedure of example 3 is repeated, the only difference being that 75 mg of activated polylactic acid (produced as described in example 1) dissolved in 8 ml of DMSO is used for the derivatization reaction.

EXAMPLE 6

Preparation of a Membrane Based on Collagen Derivatized at 20% with Polylactic Acid The procedure of example 3 is repeated, with the differences that 21.5 mg of activated polylactic acid in 6 ml of DMSO is used for the derivatization reaction, and that the PLA is activated with CDI, as described in example 2.

EXAMPLE 7

Preparation of a Membrane Based on Collagen Derivatized at 50% with Polylactic Acid The procedure of example 6 is repeated, the only difference being that 54 mg of activated polylactic acid (produced as described in example 2) dissolved in 6 ml of DMSO is used for the derivatization reaction.

EXAMPLE 8

Preparation of a Membrane Based on Chitosan Derivatized at 10% with Polylactic Acid A chitosan felt/tissue with dimensions of about 25 cm² and with a thickness of about 2 mm, weighing 150 mg, is placed in a glass Petri dish. In a 10-ml glass test tube, 17 mg of activated polylactic acid (produced as described in example 1) is dissolved in 6 ml of DMSO. The solution is added directly on the surface of the chitosan felt/tissue in the Petri dish. The dish is closed and put in a stove at 40° C. and it is left to react for 4 hours. The dish is then taken out of the stove and the felt/tissue is removed, and is immersed in a 500-ml glass beaker containing 300 ml of physiological saline at 0.9% NaCl. It is stirred gently for 2 hours. The operation is repeated once, stirring gently for 4 hours, and twice more using purified water instead of physiological saline. The felt/tissue is removed and is left to dry in the stove at 37° C. for 24-48 hours.

EXAMPLE 9

Preparation of a Membrane Based on Fibrin Derivatized at 20% with Polylactic Acid A membrane in lyophilized form based on fibrin with dimensions of about 15 cm² and with a thickness of about 3 mm, weighing 250 mg, is placed in a glass Petri dish. In a 10-ml glass test tube, 50 mg of activated polylactic acid (produced as described in example 2) is dissolved in 6 ml of DMSO. The solution is added directly on the surface of the fibrin membrane in the Petri dish. The dish is closed and is put in a stove at 40° C. and it is left to react for 4 hours. The dish is then taken out of the stove and the membrane is removed, and is immersed in a 500-ml glass beaker containing 300 ml of physiological saline at 0.9% NaCl. It is stirred gently for 2 hours. The operation is repeated once, stirring gently for 4 hours, and twice more using purified water instead of physiological saline. The felt/tissue is removed and is left to dry in the stove at 37° C. for 24-48 hours.

The invention claimed is:

1. Composite biomaterial comprising a tridimensional structure made of a polymer chosen among collagen, fibrin and chitosan, the tridimensional structure having a first surface and a second surface opposite to the first surface, the second surface conjugated with chains of a semi-synthetic polyester obtained from polymerization or copolymerization of at least a hydroxyacid chosen among lactic acid, glycolic acid or mixtures thereof,
wherein the tridimensional structure forms a first portion having a first porosity and the chains of the semi-synthetic polyester form a second portion having a second porosity, and wherein the first porosity has first pores sized to permit entry of cells into the first portion and the second porosity has second pores sized to prevent entry of cells into the second portion, wherein said cells are selected from the group consisting of skin fibroblasts and cartilage cells.

2. The composite biomaterial according to claim 1, in which the derivatization degree of the polymer forming said tridimensional structure with the polyester is comprised between 1 and 50%.

3. The composite biomaterial according to claim 2, in which said derivatization degree is comprised between 5 and 30%.

4. A medical or surgical device made of a composite biomaterial comprising a tridimensional structure made of a polymer chosen among collagen, fibrin and chitosan, the tridimensional structure having a first surface and a second surface opposite to the first surface, the second surface conjugated with chains of a semi-synthetic polyester obtained from polymerization or copolymerization of at least a hydroxyacid chosen among lactic acid, glycolic acid or mixtures thereof,
wherein the tridimensional structure forms a first portion having first porosity and the chains of the semi-synthetic polyester form a second portion having a second porosity, wherein the first porosity has first pores sized to permit entry of cells into the first portion and the second porosity has second pores sized to prevent entry of cells into the second portion, wherein the medical or surgical device is in the form of membrane or felt, wherein said cells are selected from the group consisting of skin fibroblasts and cartilage cells.

5. The device according to claim 4, in which to said biomaterial is associated at least a compound having biological or pharmacological activity.

6. The device according to claim 5 in which said compound having biological or pharmacological activity is chosen among antimicrobial activity agents, antifungal activity agents, antibiotic activity agents and growth factors.

7. The device according to claim 6 in which said antifungal activity agents and antibiotic activity agents are peptide or lipopeptide compounds.

8. The device according to claim 6 in which said growth factors are of the glycoprotein-based kind.

9. The device according to claim 4 further comprising, embedded in the tridimensional structure of the composite biomaterial, at least a broad-spectrum antibiotic.

10. The device according to claim 5 further comprising, embedded in the tridimensional structure of the composite biomaterial, at least a broad-spectrum antibiotic.

11. The device according to claim 6 further comprising, embedded in the tridimensional structure of the composite biomaterial, at least a broad-spectrum antibiotic.

12. The device according to claim 7 further comprising, embedded in the tridimensional structure of the composite biomaterial, at least a broad-spectrum antibiotic.

13. The device according to claim 8 further comprising, embedded in the tridimensional structure of the composite biomaterial, at least a broad-spectrum antibiotic.

* * * * *